United States Patent [19]

Müller et al.

[11] Patent Number: 4,946,869

[45] Date of Patent: * Aug. 7, 1990

[54] AVAROL, PROCESS FOR ITS PRODUCTION, PHARMACEUTICAL COMPOSITIONS THEREOF, AND ANTIVIRAL USE OF THE SAME

[75] Inventors: Werner E. G. Müller, Wiesbaden-Biebrich; Rudolf K. Zahn, Wiesbaden; Eckart Eich, Mainz, all of Fed. Rep. of Germany

[73] Assignee: Merz and Co. GmbH & Co., Frankfurt, Fed. Rep. of Germany

[*] Notice: The portion of the term of this patent subsequent to May 17, 1990 has been disclaimed.

[21] Appl. No.: 820,440

[22] Filed: Jan. 17, 1986

[51] Int. Cl.$^5$ ............................................. A61K 31/045
[52] U.S. Cl. ....................................................... 514/729
[58] Field of Search ........................................... 514/729

[56] References Cited

PUBLICATIONS

Comp. Biochem. Physiol. 71B, pp. 281–283 (1982).
Tetrahedon Letters 38, pp. 3401–3404 (1974) by Pergamon Press.
Experientia 38, p. 896 (1982).
Chemical Abstracts 97, p. 462, item 91:21000t (1982).
Kurelec, B., et al., "Antimutagenic activity of the novel antileukemic agents, avarone and avarol", Mutation Research, 144 (1985) pp. 63–66.
Müller, W. E. G., "Potent Antileukemic Activity of the Novel Cytostatic Agent Avarone and its Analogues in Vitro and in Vivo", Cancer Research 45 (1985) pp. 1–5.
Müller, W. E. G., et al., "Avarol, a Cytostatically Active Compound from the Marine Sponge *Dysidea Avara*", Comp. Biochem, Physiol. 80C No. 1, (Jan. 31, 1985) pp. 47–52.
Müller, W. E. G., et al., J. Antibiotics 37, 239 (1984).
Cariello, L., et al., "Developmental Aberrations in Sea-Urchin Eggs Induced by Avarol and Two Cogeners, the Main Sesquitterpenoid Hydroquinones from the Marine Sponge, *Dysidea Avara*", Comp. Biochem, Physiol., 65C, pp. 37–41 (1980).

*Primary Examiner*—Jerome D. Goldberg
*Attorney, Agent, or Firm*—Gordon W. Hueschen

[57] ABSTRACT

The antiviral compond avarol, a process for its production, pharmaceutical compositions containing said compound, and a method of combating viruses therewith, are disclosed.

3 Claims, No Drawings

AVAROL, PROCESS FOR ITS PRODUCTION, PHARMACEUTICAL COMPOSITIONS THEREOF, AND ANTIVIRAL USE OF THE SAME

BACKGROUND OF INVENTION

1. Field of Invention

Antiviral compositions comprising avarol and method of employing avarol for its antiviral activity; method of killing virus therewith; method of production of the active principle avarol. In brief, pharmaceutical compositions embodying avarol, method of treating with avarol, and employment of the said active principle for its antiviral activity.

2. Prior Art

Avarone and its hydroquinone derivative avarol are natural substances found in the marine sponge Dysidea avara (L. Minale, R. Riccio and G. Sodano, Tetrahedron Letters 1974, 3401–3404; S. de Rosa, L. Minale, R. Riccio and G. Sodano, J. Chem. Soc. Perkin I, 1408–1414 (1976)). These compounds were isolated from a diethyl ether extract using column chromatography on silica gel (L. Cariello, M. de Nicola Giudici and L. Zanetti, Comp. Biochem. Physiol. 65c, 37–41 (1980)). With regard to biological effects it has so far only been known that avarol in very high concentrations (130 μm) affects the cells of the sea urchin embryo; causing "developmental abberations" (L. Cariello et al., ibid.). The derivatives described in the literature are, among others, the 3′-methylamino and the 4′-methylaminoavarone (G. Cimino, S. de Rosa, S. de Stefano, L. Cariello and L. Zanetti, Experientia 38, 896 (1982) as well as the avarol dimethyl ether and the avarol diacetate (S. de Rosa et al., ibid.).

THE PRESENT INVENTION

It has now been found that avarol has pronounced and unpredictable antiviral properties. Owing to the aforementioned properties, this substance is suited for the treatment of viral diseases, either as such or in the form of a prodrug or precursor or any of the foregoing in the form of a pharmaceutical composition where present together with a pharmaceutically-acceptable diluent or carrier.

OBJECTS OF THE INVENTION

It is an object of the present invention to provide novel pharmaceutical compositions embodying avarol or a pro-drug or precursor thereof or therefor. It is a further object of the invention to provide a novel method of treating, eliminating, alleviating, palliating, or ameliorating undesirable viral infectious conditions by the employment of avarol or a pharmaceutical composition containing the same. An additional object of the invention is the provision of a process for producing the active principle avarol. Still additional objects will become apparent hereinafter, and still further objects will be apparent to one skilled in the art.

SUMMARY OF THE INVENTION

What we therefore believe to be comprised by our invention may be summarized inter alia in the following words:

A pharmaceutical composition suitable for use as an antiviral composition comprising an effective antiviral avarol together with a pharmaceutically-acceptable pharmaceutical carrier; also a method of combating a virus comprising administering to the host or situs an effective antiviral amount of avarol; and such a method wherein the compound is administered in the form of a pharmaceutical composition thereof, in which it is present together with a pharmaceutically-acceptable carrier or diluent. Finally a pharmaceutical composition suitable for use as an antiviral composition comprising an effective antiviral amount of avarol together with a pharmaceutically-acceptable pharmaceutical carrier and a method of combating a virus comprising administering to the host or situs an effective antiviral amount avarol.

IDENTITY

The active antiviral ingredients or agents of the present invention have the formulas:

2-[(1R)-1,2,3,4,4a,7,8,8aα-octahydro-1β,2β,4aβ,5-tetramethyl-1-naphthylmethyl]-quinone

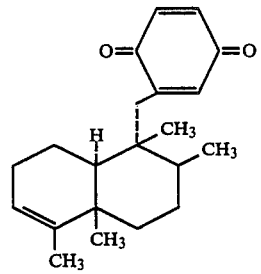

Formula o Avarone
$C_{21}H_{28}O_2$; Mol wt: 312.20
C 80.73%; H 9.03%; O 10.24%

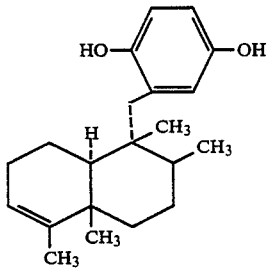

Its derivative Avarol
$C_{21}H_{30}O_2$; Mol wt: 314.22
C 80.32%; H 9.81%; O 9.87%

HISTORY

Sponges live in symbiosis with algae, fungi, bryozoae and bacteria (Muller et al, F. Bacteriol. 1981, 145, pp. 548–558). Experimental data support the hypothesis that the symbiotic relationship between sponge and non-sponge cells is based on a growth-promoting (e.g., lectin) and a growth-inhibiting principle (cytostatic agent). One derivative of the cytostatic agent 1-β-D-arabinofuranosylthymine, isolated from the sponge Cryptothethya crypta, has already been established as an anti-cancer agent in the clinic (1-β-D-arabinofuranosylcytosine) (Muller et al., Jap. J. Antibiotics 1977, 30 Supp. pp. S104–S120). In the course of our screening program for antimitotic agents, it was found that the sponge secondary metabolites Avarone and Avarol exhibit antimitotic activity, which is different than that of Vincristine [Oncovin ®], Colchicine, or 4′-Demethylepipodophyllotoxin-9-(4,6-0-ethylidene-β-D-glucopyranoside) [Etoposide ®].

ISOLATION AND SYNTHESIS

Avarol has been isolated from the marine sponge Dysidea avara, which is ubiquitous near the Atlantic coast of Europe, in the Mediterranean and around the Maldive Islands (Minale et al., Tetrahedron Lett. 1974, No. 36, pp. 3401-3404). According to our present process, ground, chopped, or otherwise comminuted material is extracted with ethyl acetate. The organic phase is dried over $MgSO_4$ and then evaporated to dryness yielding a tar-like residue. This material is taken up in benzene and purified by silica gel column chromatography using benzene/10% ethyl acetate as solvent. The Avarol fractions are concentrated; purified Avarol is obtained after several crystallizations from acetone-methylene chloride. Yield: 2.7 g of Avarol from 1 kg of fresh material. Avarone may be obtained from its corresponding hydroquinone Avarol by $Ag_2O$ oxidation, but it is preferably obtained by column separation according to our new process, represented by Example 1 hereinafter.

DESCRIPTION

Avarone: Yellowish-brownish crystals; m.p. 62°-64° C. (hexane); slightly soluble in water; solubility in dimethylsulfoxide>100 mg/ml at 23° C.; stable in solution when stored at 4° C. for up to 1 year.

Avarol: Whitish crystals; m.p. 146°-148° C. (chloroform); other characteristics same as for Avarone.

PRODRUGS OR PRECURSORS AND THEIR PREPARATION

The compounds avarone and avarol may also be employed or embodied in pharmaceutical compositions according to the invention in the form of compounds which convert to avarone or avarol after administration to the living animal body. Such compounds are commonly referred to today as prodrugs or precursors, and representative examples include esters of avarol and alkylamino derivatives of avarone. As already indicated, some of these compounds are known in the prior art, whereas others are made in a known manner corresponding thereto. Representative of such prodrugs and precursors, and their preparation, are set forth in the following.

The active ingredients of the present invention, and their precursors or prodrugs, are accordingly avarone, avarol, and their derivatives of the general formula I

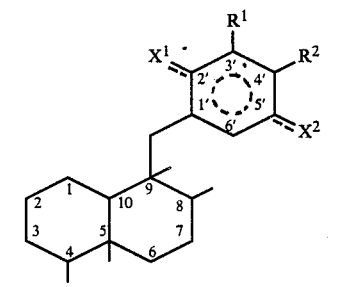

wherein

1. $X^1$ and $X^2$ is oxo with double bonds between C-1′ and C-6′, and between C-3′ and C-4′;

$R^1$ is hydrogen and
   $R^2$ is alkyl amino having one, two, three or four C atoms;

or wherein

2. $X^1$ and $X^2$ is oxo with double bonds between C-1′ and C-6′, and between C-3′ and C-4′;
   $R^1$ is alkyl amino having one, two, three or four C atoms, and
   $R^2$ is hydrogen;

or wherein

3. $X^1$ and $X^2$ is hydroxy or acyloxy with 2-6 C atoms or $X^1$ with $X^2$ is diacyloxy with 4-6 C atons with aromatic ring: and
   $R^1$ and $R^2$ is hydrogen, 4. Avarone—As in 1 or 2, but both $R^1$ and $R^2$ being hydrogen, and 5. Avarol—As in 3, both $X^1$ and $X^2$ being hydroxy, as well as salts of the alkylaminoavarones as conventionally obtained by reaction with physiologically-tolerable acids.

The compounds of formula I thus comprise avarone ($R^1=R^2=H$ in Formula Ia) and alkylaminoavarone derivatives thereof, as well as avarol ($R^1=R^2=H$ in Formula Ib) and esters thereof.

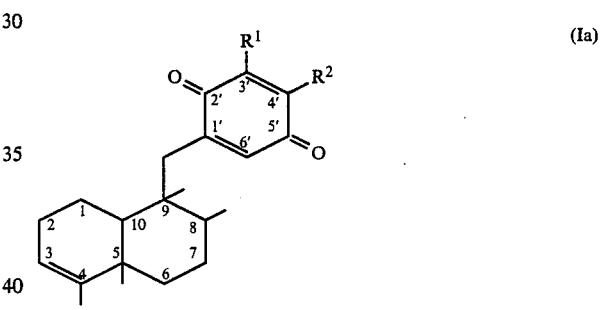

(Ia)

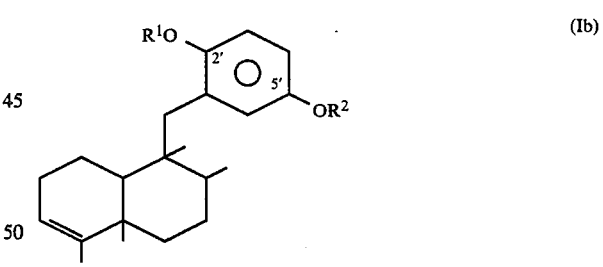

(Ib)

The process for the manufacture of alkylaminoavarones of the general formula Ia is characterized in that avarone is reacted with alkylamine hydrochloride of the general formula $RNH_2 \times HCl$, the resulting compounds being converted, if desired, into salts using physiologically-tolerable acids. Compounds of the general formula $RNH_2 \times HCl$ can be ethyl, propyl, isopropyl, n-butyl, isobutyl and tert. butylamine hydrochloride (Reaction 1 hereinafter).

Preparation of avarone derivatives of the general formula Ia by placing the substituent —NHR in 3′ or 4′ position is characterized in that the reaction components are reacted in 50% ethanol in the presence of pyridine (G. Cimino, S. de Rosa, S. de Stefano, L. Cariello and L. Zanetti, Experientia 38, 896 (1982)). The resulting isomer mixtures of 3′ and 4′ alkylamino avarones can be separated by column chromatography using silica gel. If desired, these reaction products can be converted into their salts by reaction with physiologically tolerable acids. For this purpose suitable acids are hydrochloric acid, hydrobromic acid, sulphuric acid, phosphoric acid, tartaric acid, maleic acid, etc.

The process for the manufacture of avarol derivatives of the general formula Ib, wherein $R^1$ and $R^2$ are acyl, is characterized in that avarol is acylated with an acyl chloride of the general formula RCOCl or with a carboxylic acid anhydride of the general formula RCOO-COR, with the exception of the acetanhydride at the hydroxyl group of the C-2' and/or C-5' position. For this purpose acid chlorides or acid anhydrides of dibasic acids such as, e.g., succinic acid, can be used, whereby one molecule of avarol accounts for only one molecule of the derivative of the dibasic acid (diacyloxy).

Compounds of the general formula RCOCl can be, for example, straight-chain acylchlorides such as acetyl, propionyl, n-butyryl, n-valeroyl and capronoyl chlorides, as well as branched acyl chlorides like isobutyryl, isovaleroyl, or ethylmethylacetyl, and trimethyl acetyl chloride. Compounds of the general formula RCOO-COR can, for example, be straight-chain acid anhydrides such as propionic acid, butyric acid, valeric acid and capronic acid anhydrides as well as branched acid anhydrides like isobutyric acid, valeric acid, or ethylmethyl acetic acid and trimethyl acetic acid anhydrides (Reaction 2 hereinafter).

The preparation of the avarol derivatives of the general formula Ib by introducing substituent —COR is characterized in that the reaction components are reacted in the presence of pyridine (S. de Rosa, L. Minale, R. Riccio and G. Sodano, J. Chem. Soc. Perkin I. 1976, 1408-1414; Organikum, VEB Deutscher Verlag der Wissenschaften, 13th Edition, Berlin 1974, pp. 441-446).

REACTION 1

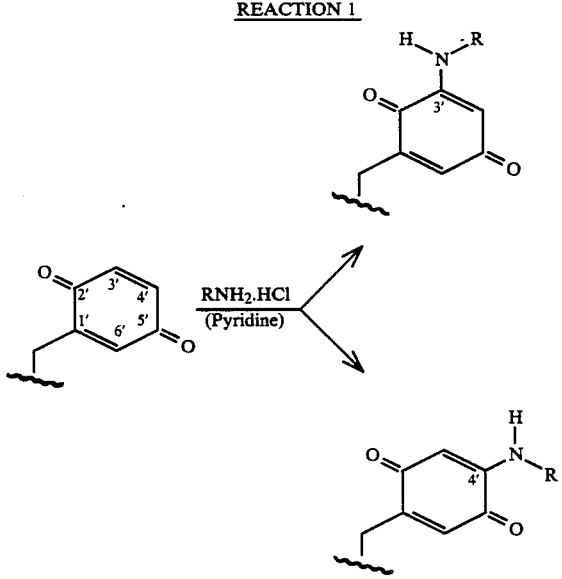

REACTION 2

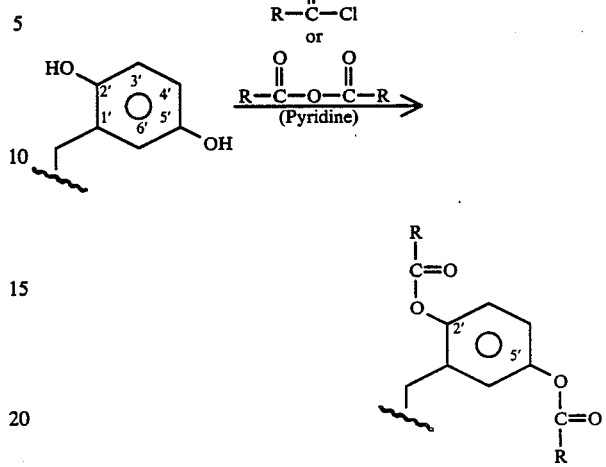

PREPARATION

Preparation of the active principles avarone and avarol of the present invention from known starting materials is effected according to the following specific Examples and pursuant to the following general procedure.

Accordingly, additional subject matter of the invention comprises a process for the manufacture of avarone and avarol characterized in that the fresh marine sponge *Dysidea avara* is ground, cut into small pieces, or otherwise comminuted, and then extracted with ethyl acetate, solvent being removed from the extract, which extract is preferably reduced to dryness, and the residue being chromatographed over a silica gel column using suitable solvent systems for separating the diketone (hydroquinone) compound from the aromatic diol, such as benzene/ethyl acetate or the like, including, for example, an aromatic solvent such as benzene or an aliphatic solvent such as hexane, together with up to about twenty percent (V/V) of an aliphatic solvent such as diethylether or ethylacetate. By the employment of this method avarone and avarol can be conveniently separated and isolated.

DETAILED DESCRIPTION OF THE INVENTION

The following Examples are given for purposes of illustration only, but are not to be construed as limiting.

Examples 2a to 2d of the following examples were obtained according to Reaction 1, whilst examples 3 to 4 were prepared according to Reaction 2. Example 1 relates to the preparation of avarone and avarol from the natural product.

EXAMPLE 1

Avarone and Avarol

Extract 3 kg of the sponge with 250 ml of ethyl acetate. Dry the resultant extract over magnesium sulfate and filter. Evaporate the filtrate to dryness. Take up the residue in benzene and subject to chromatography using a silica gel column and benzene as extraction agent. Avarone can be found in the extract whilst avarol is retained on the column. Extract avarol with a mixture of benzene and ethyl acetate (90:10, V:V). Evaporate the extract to dryness. Subsequently, pure avarol is obtained by crystallization from dichloromethaneacetone. Purify avarone by recrystallization from benzene.

| Avarone | Avarol |
|---|---|
| Melting point: 62–64° C. | Melting point: 146–148° C. |

EXAMPLE 2

3'-ethylamino avarone and 4'-ethylamino avarone (a) Add 2.5 g of ethylamino hydrochloride and 5 ml of pyridine to a solution of 500 mg avarone in 1000 ml of 50% ethanol, and distill off the ethanol under water-jet vacuum after 20 hours. Extract the aqueous residue with dichloromethane and chromatograph the reduced dichloromethane extract using a silica gel column and dichloromethane as extraction agent. In the course of this process 3'-ethylamino and 4'-ethylamino avarone is obtained.

In the same way following products have been obtained:
(b) 3'-propylamino and 4'-propylamino avarone
(c) 3'-isopropylamino and 4'-isopropylamino avarone
(d) 3'-n-butylamino and 4'-n-butylamino avarone

EXAMPLE 3

Avarol Diacetate (a) Dissolve 500 mg of avarol in 20 ml of absolute pyridine, and add 1 g of acetyl chloride in portions to the solution under shaking. Treat the mixture as usual, evaporate to dryness and extract the residue with boiling heptane. On cooling the ester crystallizes. It is then recrystallized from hexane.

Melting point: 62°–64° C.

In the same way the following products have been obtained:
(b) Avarol dipropionate
(c) Avarol divalerianate
(d) Avarol ditrimethyl acetate

EXAMPLE 4

Avarol Dicapronate (a) Dissolve 300 mg of avarol in 25 ml of absolute pyridine, and add 0.6 g of caproic acid anhydride in portions to the solution whilst shaking. Treat the mixture as usual, evaporate to dryness, and extract the residue with boiling heptane. Recrystallize from acetone and subsequently from hexane.

In the same way the following products have been obtained:
(b) Avarol diisovalerianate
(c) Avarol diethyl methyl acetate
(d) Avarol succinate

PHARMACEUTICAL COMPOSITIONS

The active ingredients of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use; in the form of suppositories for rectal administration; or in the form of sterile injectable solutions for parenteral (including intravenous or subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredient or, more broadly, ten (10) to one hundred (100) milligrams, per tablet, are accordingly suitable representative unit dosage forms.

METHOD OF TREATING

Due to their high degree of activity and their low toxicity, together presenting a most favorable therapeutic index, the active principles of the invention may be administered to a subject, e.g., a living animal body, in need thereof, for the treatment, alleviation, or amelioration, palliation, or elimination of an indication which is susceptible thereto, or representatively of an indication set forth elsewhere in this application, preferably concurrently, simultaneously, or together with a pharmaceutically-acceptable carrier or diluent, especially and preferably in the form of a pharmaceutical composition thereof, whether by oral, rectal, or parental (including intravenous and subcutaneous) or in some cases even topical route, in an effective antiviral amount. Suitable dosage ranges are 1–1000 milligrams daily, preferably 10–500 milligrams daily, and especially 50–500 milligrams daily, depending as usual upon the exact mode of administration, form in which administered, the indication toward which the administration is directed, the subject involved and the body weight of the subject involved, and the preference and experience of the physician or veterinarian in charge.

EXAMPLES OF REPRESENTATIVE PHARMACEUTICAL COMPOSITIONS

With the aid of commonly used solvents auxiliary agents and carriers, the reaction products can be processed into tablets, coated tablets, capsules, drip solutions, suppositories, injection and infusion preparations, and the like and can be therapeutically applied by the oral, rectal parenteral and additional routes. Representative pharmaceutical compositions follows.

(a) Tablets suitable for oral administration which contain the active ingredient may be prepared by conventional tabletting techniques.

(b) For suppositories, any usual suppository base may be employed for incorporation thereinto by usual precedure of the active ingredient, such as a polyethyleneglycol which is a solid at normal room temperature but which melts at or about body temperature.

(c) For parental (including intravenous and subcutaneous) sterile solutions, the active ingredient together with conventional ingredients in usual amounts are employed, such as sodium chloride, sodium dihydrogen phosphate, disodium edetate (ethylenediaminetetraacetic acid disodium salt), benzyl alcohol, sodium hydroxide to adjust pH, and double-distilled water q.s., according to conventional procedure, such as filtration, aseptic filling into ampoules or IV-drip bottles, and autoclaving for sterility.

Other suitable pharmaceutical compositions will be immediately to one skilled in the art.

The following examples are again given by way of illustration only and are no to be construed as limiting.

EXAMPLE 1

Tablet Formulation

A suitable formulation for a tablet containing 10 milligrams of active ingredient is as follows:

|  | Mg. |
|---|---|
| Active Ingredient | 10 |
| Lactose | 18 |
| Potato starch | 38 |
| Gelatin | 2 |
| Talcum | 2 |
| Magnesium stearate | 0.1 |

EXAMPLE 2

Tablet Formulation

Another suitable formulation for a tablet is as follows:

|  | Mg. |
|---|---|
| Active Ingredient | 10 |
| Potato starch | 40 |
| Polyvinylpyrrolidone | 5 |
| Sugar coated and colored. | |

EXAMPLE 3

Capsule Formulation

A suitable formulation for a capsule containing 10 milligrams of active ingredient is as follows:

|  | Mg. |
|---|---|
| Active Ingredient | 10 |
| Corn starch | 90 |
| Lactose | 50 |
| Talcum | 2 | filled in a gelatin capsule.

EXAMPLE 4

Solution for injection

A suitable formulation for an injectable solution containing one percent of active ingredient is as follows:

| Active Ingredient | mg | 12 |
|---|---|---|
| Sorbitol | mg | 40 |
| Sterile water to make | ml | 1 |

EXAMPLE 5

Liquid oral formulation

A suitable formulation for 1 liter of a liquid mixture containing 2 milligrams of active ingredient in one milliliter of the mixture is as follows:

|  | G. |
|---|---|
| Active Ingredient | 2 |
| Saccharose | 250 |
| Glucose | 300 |
| d-Sorbitol | 150 |
| Agar-agar | 0.15 |
| Methylparaben | 0.5 |
| Propylparaben | 0.05 |
| Orange flavor | 10 |
| Tartrazine yellow. | |
| Purified water to make a total of 1000 ml. | |

EXAMPLE 6

Liquid oral formulation

Another suitable formulation for 1 liter of a liquid mixture containing 2 milligrams of active ingredient in one milliliter of the mixture is as follows:

|  | G. |
|---|---|
| Active Ingredient | 2 |
| Tragacanth | 7 |
| Glycerol | 50 |
| Saccharose | 400 |
| Methylparaben | 0.5 |
| Propylparaben | 0.05 |
| Black currant-flavor | 10 |
| Red No. 2 C.I. 184 | 0.02 |
| Purified water to make a total of 1000 ml. | |

EXAMPLE 7

Liquid oral formulation

Another suitable formulation for 1 liter of liquid mixture containing 2 milligrams of active ingredient in one milliliter of the mixture is as follows:

|  | G. |
|---|---|
| Active Ingredient | 2.4 |
| Saccharose | 400 |
| Bitter orange peel tincture | 20 |
| Sweet orange peel tincture | 15 |
| Purified water to make a total of 1000 ml. | |

PHARMACOLOGY—SUMMARY

The active principles of the present invention, avarone and avarol, and pharmaceutical compositions thereof and method of treating therewith, are characterized by unique advantageous and unpredictable properties, rendering the "subject matter as a whole", as claimed herein, unobvious. The compounds and pharmaceutical compositions thereof have exhibited, in standard accepted reliable test procedures, the following valuable properties and characteristics:
Antiviral
and are accordingly of utility in the treatment, elimination, palliation, alleviation, and amelioration of responsive conditions, infections, and infestations by application or administration to the host or to the situs, or even to the microorganism itself, as when viral infestations are involved.

PHARMACOLOGY

Avarol and its derivatives show an antiviral effect in BHK cell cultures that have been infected with herpes simplex virus of types I and II. The viral concentration (multiplicity of infectiosity) was adjusted to 0.5 to 1.5 plaque forming units per cell. 2 hours after infection the cultures were washed, and the reaction products added. 24 hours after infection the virus titre (p.f.u./0.2 ml) was determined. With concentrations of, e.g., avarol of 1

μm type I replication of $9\times10^4$ (control) was reduced to $1\times10^3$ (treated cultures), and type II replication of $6\times10^5$ (control) was diminished to $7\times10^3$ (treated cultures).

Owing to the pronounced antiviral activity of avarol, it is clear that it will be useful in the treatment of infectious diseases. TOXICITY The in vivo toxicity (mg compound/kg) of Avarol on male NMRI mice is as follows; acute toxicity: $LD_{50}$ 181.2 (269.2), $LD_{10}$111.1 (156.4) and subacute toxicity: $LD_{50}$172.1 (218.4), $LD_{10}$109.7 (138.6) ( Muller et al., Cancer Research 1985, 45 (10), in press).

PHARMACOLOGICAL ACTIONS—ANTIVIRAL

The antiviral activity of Avarol is not restricted to DNA containing viruses only, but is also pronounced towards RNA containing viruses. The compound inhibits sensitively the growth of oncogenic RNA viruses.

The studies were performed with Schmidt-Ruppin D strain of Rous Sarcoma Virus (RSV) in cell culture assays. the detailed methods for testing the compounds were described earlier in (A. Totsuka, W.E.B. Muller and R.K. Zahn: Bleomycin, action on growth of oncogenic RNA viruses and on cell transformation. Archives of Virology 43, 169–179; 1975). For infection, secondary cultures of chick embryo fibroblasts were used. The cells infected with RSV at a concentration of $10^{-3}$ focus forming units (FFU). One hour later the cultures were supplemented with different concentrations of the test compound. 48 hours later the virus yield per cell was determined.

Result: At a concentration of: 1 micromolar of Avarol by 68%.

The virus yield in the infected cultures, which were not treated by the compounds, was 251,188 FFU per 1,000,000 cells.

The proliferation of non-infected cells was not influenced by Avarol at the concentrations (1 micromolar) used.

The described inhibition of oncogenic RNA viruses in intact cell system is also confirmed by subcellular studies. As a testing parameter, the key enzyme for virus multiplication—the reverse transcriptase (RNA-dependent DNA polymerase)—was chosen. This enzyme was isolated from Rauscher murine leukemia virus (RMLV) and from human T-lymphotropic retrovirus (HTLV-III) as described earlier (W.E.G. Muller R.K. Zahn, H.J. Seidel: Inhibitors acting on nucleic acid synthesis in an oncogenic RNA virus. Nature, New Biology 232 143–145; 1971). The detailed description of the test procedure of the reverse transcriptase is given in the same publication.

Results: At a concentration of 1 microgram per ml the reverse transcriptase from RMLV was inhibited by 59% and the same enzyme from HTLV-III by 67%.

In conclusion, from the foregoing, it is apparent that the present invention provides novel, valuable, and unpredictable applications and uses of the compound Avarol, which compound comprises the active principle according to the present invention, as well as novel pharmaceutical compositions thereof and methods of preparation thereof and of treating therewith, all possessed of the foregoing more specifically-enumerated characteristics and advantages.

The high order of activity of the active agent of the present invention and compositions thereof, as evidenced by the tests reported, is indicative of utility based on its valuable activity in human beings as well as in lower animals. Clinical evaluation in human beings has not been completed, however. It will be clearly understood that the distribution and marketing of any compound or composition falling within the scope of the present invention for use in human beings will of course have to be predicated upon prior approval by governmental agencies, such as the U.S. Federal Food and Drug Administration, which are responsible for and authorized to pass judgment on such questions.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. A pharmaceutical composition in the form of tablets, capsules, emulsions, elixirs, suppositories, or sterile injectable solutions, suitable for an antiviral composition comprising an effective antiviral amount of avarol together with a pharmaceutically-acceptable pharmaceutical carrier.

2. A method of combating a virus susceptible thereto comprising administering to a living animal host an effective antiviral amount of avarol.

3. A method of claim 2, wherein avarol is administered in the form of a pharmaceutical composition thereof, in which it is present together with a pharmaceutically-acceptable carrier or diluent.

* * * * *

UNITED STATES PATENT AND TRADEMARK OFFICE
CERTIFICATE OF CORRECTION

PATENT NO. : 4,946,869

DATED : August 7, 1990

INVENTOR(S) : Werner E. G. Müller, Rudolf K. Zahn and Eckart Eich

It is certified that error appears in the above-identified patent and that said Letters Patent is hereby corrected as shown below:

Title Page, [45]; delete the "*" preceding "August 7, 1990"
(No Disclaimer has been filed in this application)

Title Page, the entry following "[73] Assignee:"; delete the entire entry
"[*] Notice: The portion of the term of this patent subsequent to May 17, 1990 has been disclaimed."
(No Disclaimer has been filed in this application)

Signed and Sealed this

Twenty-ninth Day of January, 1991

Attest:

HARRY F. MANBECK, JR.

*Attesting Officer*      *Commissioner of Patents and Trademarks*

UNITED STATES PATENT AND TRADEMARK OFFICE
CERTIFICATE OF CORRECTION

PATENT NO. : 4,946,869

DATED : August 7, 1990

INVENTOR(S) : Werner E. G. Müller, Rudolf K. Zahn, Eckart Eich

It is certified that error appears in the above-identified patent and that said Letters Patent is hereby corrected as shown below:

Column 1, line 65/66; "antiviral avarol" should read
   -- antiviral amount of avarol --.
Column 2, line 10/11; "amount avarol." should read
   -- amount of avarol --.
Column 2, line 16; "4,4α, should read -- 4,4a, --.
Column 2, line 16; "8αα- should read -- 8aα- --.
Column 2, line 16; "4αβ, should read -- 4aβ, --.
Column 2, line 31; "o" should read -- of --.
Column 4, line 14; "atons" should read -- atoms --.
Column 8, line 39; solvents auxiliary" should read·
   -- solvents, auxiliary --.
Column 8, line 44; "rectal parenteral" should read
   -- rectal, parenteral".
Column 8, line 50/51; "prece-dure" should read -- proce-dure --.
Column 8, line 55; "parental" should read -- parenteral --.
Column 8, line 68; "no" should read -- not --.
Column 11, line 7; delete "TOXICITY" after "diseases." and insert
   it in the next line as a heading.
Column 11, line 21; "the" first occurrence should read -- The --.

Signed and Sealed this

Twenty-fourth Day of December, 1991

Attest:

HARRY F. MANBECK, JR.

*Attesting Officer*  *Commissioner of Patents and Trademarks*